United States Patent [19]

Horodysky

[11] Patent Number: 4,529,529

[45] Date of Patent: Jul. 16, 1985

[54] BORATED DIHYDROCARBYLENETRIAMINE AMIDES AND LUBRICANT AND FUEL COMPOSITIONS CONTAINING SAME

[75] Inventor: Andrew G. Horodysky, Cherry Hill, N.J.

[73] Assignee: Mobil Oil Corporation, New York, N.Y.

[21] Appl. No.: 576,227

[22] Filed: Feb. 1, 1984

[51] Int. Cl.$^3$ .................. C10M 1/54; C10M 5/28
[52] U.S. Cl. .................................. 252/49.6; 564/8; 564/9; 564/141; 564/215; 260/404.5; 260/462 R; 260/413
[58] Field of Search .............. 252/49.6; 564/8, 9, 564/141, 215; 260/404.5 PA, 462 R, 413 R

[56] References Cited

U.S. PATENT DOCUMENTS

| | | | |
|---|---|---|---|
| 2,453,057 | 11/1948 | Zienty | 564/141 |
| 3,000,916 | 9/1961 | Klass et al. | 252/49.6 |
| 4,226,734 | 10/1980 | Schuster | 252/49.6 |
| 4,328,113 | 5/1982 | Horodysky et al. | 252/49.6 |

*Primary Examiner*—William R. Dixon, Jr.
*Assistant Examiner*—C. Johnson
*Attorney, Agent, or Firm*—Alexander J. McKillop; Michael G. Gilman; Van D. Harrison, Jr.

[57] ABSTRACT

Borated hydrocarbylenetriamine amides can be made by borating the appropriate reaction product of a triamine and an organic monocarboxylic acid. They demonstrate friction reducing and/or fuel consumption reducing properties when formulated into lubricants, particularly lubricating oils, and fuels.

28 Claims, No Drawings

BORATED DIHYDROCARBYLENETRIAMINE AMIDES AND LUBRICANT AND FUEL COMPOSITIONS CONTAINING SAME

CROSS REFERENCE TO RELATED APPLICATIONS

U.S. application Ser. No. 576,180, filed Feb. 1, 1984, uses the same reactants as disclosed herein, but the products disclosed are entirely diferent. The invention claimed in Ser. No. 576,180 constitutes an overborated product, i.e., one in which an *excess* of boron compound has been used.

BACKGROUND OF THE INVENTION

1. Field of the Invention

The invention relates to novel products and to their use in lubricants or liquid fuels to reduce friction and fuel consumption in internal combustion engines. More particularly, the invention relates to borated N-hydrocarbyl dihydrocarbylenetriamine amides and to lubricant and fuel compositions containing same.

2. Discussion of Prior Related Disclosures

As those skilled in this art know, additives impart special properties to lubricants. They may give the lubricants new properties or they may enhance properties already present. One property all lubricants have in common is the reduction of friction between materials in contact. Nonetheless, the art constantly seeks new materials to enhance such friction properties.

A lubricant, even without additives, when used in an internal combustion engine will not only reduce friction, but in the process will also reduce consumption of the fuel required to run it. When oils appeared to be inexhaustable, and cheap, minimum attention was given to developing additives for the specific purpose of increasing frictional properties or reducing fuel consumption. Instead, most of the advances in this area came as a result of additives being placed in lubricants for other purposes. However, recent events have added impetus to research programs designed specifically to find materials capable of enhancing the ability of a lubricant to reduce friction.

It is probably generally understood in this art that there is not necessarily a correlation between friction reducing properties of an additive and its ability to correspondingly further reduce fuel consumption in an engine. That is, one cannot predict with absolute certainty from the ability of an additive to reduce friction that it will also act to decrease fuel consumption. Thus, even though the use of amides in lubricants is known (see U.S. Pat. No. 3,884,822, for example, which discloses lubricants containing the product of reaction between an aminopyridine and oleic acid), no art teaches or suggests the amides of this invention or that they are useful for the purposes disclosed herein.

SUMMARY OF THE INVENTION

In accordance with the invention there is provided a lubricant or liquid fuel composition comprising a major proportion of a lubricant or fuel and an antifriction amount of a product of reaction between (1) a boron compound, (2) a N-hydrocarbyl dihydrocarbylenetriamine or mixture of such triamines of the formula

wherein R is hydrogen or a $C_{10}$ to $C_{30}$ hydrocarbyl group, at least one of R being the latter and $R^1$ is the same or different $C_2$ to $C_4$ hydrocarbylene group, preferably an alkylene group such as an ethylene, propylene or butylene group and (3) a carboxylic acid or acid ester having the formula

wherein $R^2$ and $R^3$ are, individually (i.e., they may be the same or different), hydrogen or a $C_1$ to $C_4$ hydrocarbyl group, including alkyl groups, i.e., a methyl, ethyl, propyl or butyl group.

As used herein, "hydrocarbyl" and "hydrocarbylene" are preferably alkyl and alkylene, respectively, but may include alkenyl and alkenylene. "Hydrocarbyl" also may include aryl, alkaryl, aralkyl and cycloalkyl groups, the aryl portions having 6 to 14 carbon atoms.

The invention also provides the products per se and a method of reducing fuel consumption in internal combustion engines by employing the disclosed fuel or lubricant compositions.

DESCRIPTION OF SPECIFIC EMBODIMENTS

In making the products in accordance with the present invention a N-hydrocarbyl dihydrocarbylenetriamine is first reacted with a boron compound and the product thus formed is reacted with a carboxylic acid or acid ester.

The compounds of the invention prepared by the method just generally described can be made simply by heating a mixture of triamine and boron compound at a temperature and for a time to form the initial product, followed by reacting the resulting product with an acid or acid ester so that part or all of the free amine groups are reacted.

The general reaction conditions are not critical. Reaction can take place between the triamine and the acid or acid ester at a temperature of between about 80° C. and about 120° C., preferably about 100° C. to about 180° C. The reaction will usually be completed in from to 10 hours, but where the reactants demand it, up to 24 hours may be required for reaction completion.

Hydrocarbon solvents, or other inert solvents may be used in the reaction. Included among the useful solvents are benzene, toluene and xylene. In general, any hydrocarbon solvent can be used in which the reactants are soluble and which can, if the products are soluble therein, by easily removed.

In carrying out the reaction, the molar ratio of triamine to acid preferably will range from about 1:1 to about 1:2.

Some of the useful triamines include N-oleyl diethylenetriamine, N-tallow diethylenetriamine, N-hydrogenated tallow diethylenetriamine, N-soya diethylenetriamine, N-coco diethylenetriamine, N-decyl diethylenetriamine, N-dodecyl diethylenetriamine, N-tetradecyl diethylenetriamine, N-octadecyl diethylenetriamine, N-eicosyl diethylenetriamine, N-triacontyl diethylenetriamine, N-oleyl dipropylenetriamine, N-tallow dipropylenetriamine, N-hydrogenated tallow dipropylenetriamine, N-soya dipropylenetriamine, N-coco dipropylenetriamine, N-decyl dipropylenetriamine, N-dodecyl dipropylenetriamine, N-tetradecyl dipropylenedtriamine, N-octadecyl dipropylenetriamine, N-eicosyl dipropylenetriamine, N-triacontyl dipropylenetriamine, the corresponding N—$C_{10}$ to $C_{30}$ hydrocarbyl dibutylenetriamine members as well as the corresponding mixed members, as for example, the N—$C_{10}$ to $C_{30}$ hydrocarbyl ethylenepropylenetriamine, N—$C_{10}$ to $C_{30}$ hydrocarbyl ethylenebutylenetriamine and N—$C_{10}$ to $C_{30}$ hydrocarbyl propylenebutylenetriamine. All the R groups mentioned are alkyl or alkenyl. Others, such as an aryl group, an alkaryl group, an aralkyl group or a cycloalkyl group, as previously mentioned, may be used in effective additives.

The boron compounds that may be used in the herein-described invention include boric oxide, metaborates, a compound of the formula

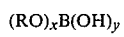

$(RO)_xB(OH)_y$ wherein R is an alkyl group containing 1 to 6 carbon atoms, x is 0 to 3 and y is 0 to 3, their sum being 3, and mixtures of any of these boron compounds. The formula embraces boric acid as well as the alkylborates, e.g., mono-, di- and trimethyl borates, mono-, di- and triethyl borates, mono-, di- and tripropyl borates, mono-, di- and tributyl borate, mono-, di- and triamyl borates and mono-, di- and trihexyl borates.

Useful acids include formic acid as the preferred member, but also include the less preferable acetic, propionic and butyric acids or mixtures of any of the four. The acid esters include, e.g., the formate esters such as methyl formate.

The reaction conditions are not critical in the boration reaction. Reaction temperatures can range from about 80° C. to about 260° C., preferably about 120° C. to 170° C. Times of reaction will generally be for from about 1 to about 20 hours.

Solvents that can be used in either step include hydrocarbon solvents such as benzene, toluene and xylene as well as alcohol solvents such as butanol and pentanol.

The temperature of reaction between the boron compound-amine product and the carboxylic acid or acid ester will range from about 100° C. to about 180° C., preferably about 80° C. to about 120° C. The time of reaction will range from about 1 to about 20 hours.

In the reaction of boron compound and triamine, sufficient boron compound is used to react from about 5% to about 95% of the available amino groups, preferably from about 25% to about 50% thereof, therewith. Further, from about 5% to about 100% of the unborated sites are reacted with the acid or acid ester. The molar ratios of initial product to the acid or acid ester should be selected accordingly.

An important feature of the invention is the ability of the additives to improve the friction qualities of oleaginous materials such as lubricating oils, which may be either a mineral oil a synthetic oil, or mixtures thereof, or a grease in which any of the aforementioned oils are employed as the vehicle. In general, mineral oils, both paraffinic, naphthenic or mixtures thereof, are employed as a lubricating oil or as the grease vehicle, they may be of any suitable lubricating viscosity range, as for example, from about 45 SSR at 100° F. to about 6000 SSU at 100° F., and preferably from about 50 to about 250 SSR at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities, i.e., at least 1% by weight thereof, to impart to the resulting grease composition the desired consistency. Included are metal soaps of hydroxycarboxylates, such as the hydroxystearates derived from 12-hydroxystearic acids, esters or glycerides, especially the lithium or calcium hydroxystearate. Often preferred is lithium 12-hydroxystearate. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils are desired, various classes of oils may be successfully utilized. Typical synthetic vehicles include polyisobutylenes, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl) ether, phenoxy phenylethers. In preparing greases using synthetic oils, thickeners known to the art (including some of those mentioned hereinabove) can be used.

It is to be understood that the lubricant compositions contemplated herein can also contain other materials. For example, other corrosion inhibitors, extreme pressure agents, viscosity index improvers, coantioxidants, antiwear agents and the like can be used. These include, but are not limited to, phenates, sulfonates, succinimides, zinc dialkyl dithiophosphates, and the like. These materials do not detract from the value of the compositions of this invention; rather the materials serve to impart their customary properties to the particular compositions in which they are incorporated. In particular, the frictional and high temperature stabilizing properties of the compositions of this invention may be enhanced by the incorporation of from about 0.1% to about 2% by weight of metal phosphorodithioates, particularly zinc dialkyl dithiophosphates, made from low to moderate molecular weight alcohols such as propanol, butanol, pentanol, hexanol, octanol and the like, and mixtures thereof.

The products of this invention can also be employed in liquid hydrocarbon fuels, alcohol fuels or mixtures thereof, including mixtures of hydrocarbons, mixtures of alcohols and mixtures of hydrocarbon and alcohol fuels to reduce friction and improve fuel economy. About 25 pounds to about 500 pounds or preferably about 50 to 100 pounds, of amide per thousand barrels of fuel for internal combustion engines may be used. Liquid hydrocarbon fuels include gasoline, gasahol, fuel oils and diesel oils. Methyl and ethyl alcohols are examples of alcohol fuels. Other additives such as fuel dispersants, carburetor, detergents, stabilizers, antirust agents, demulsifiers metal deactivators, intake manifold detergents, dyes and the like can be used with our friction reducers in the fuel compositions.

In general, the reaction products of the present invention may be employed in any amount which is effective for imparting the desired degree of friction reduction and resulting fuel economy improvement and/or antioxidant activity. In lubricant applications, the product is effectively employed in amounts from about 0.05% to about 10% by weight, and preferably from about 0.5% to about 5% of the total weight of the composition.

The following Examples will present illustrations of the invention. They are illustrative only, and are not meant to limit the invention.

EXAMPLE 1

Approximately 216 g of N-tallow-dipropylenetriamine (obtained as Armosperse 300 from Armak Chemical Co.), 100 g of toluene and 8 g of boric acid were reacted as generally described in Example 1. The reactor contents were heated to 160° C. for a period of 4½ hours until water evolution during azeotropic distillation ceased. The solvent was removed by azeotropic distillation. The intermediate was cooled to 130° C. and filtered through diatomaceous earth.

EXAMPLE 2

Approximately 100 g of the partially borated N-tallow-dipropylenetriamine reaction product of Example 3 were charged to a 500 ml reactor equipped with heater, agitator, Dean-Stark tube with condenser and a means to blanket the vapor space with nitrogen. Approximately 100 g of toluene and 13 g of 88% formic acid were added and the reactor contents were heated up to 120° C. for a period of 3 hours. The reactor was heated to 160° C. over a period of 3½ hours until wate evolution during azeotropic distillation ceased. The crude product was vacuum topped to remove solvent and other volatiles. The product was an amber liquid which became waxy after cooling.

EVALUATION OF THE COMPOUNDS

The compounds were evaluated in Low Velocity Friction Apparatus (LVFA) in a fully formulated mineral or synthetic, automative engine oil containing an additive package including antioxidant, dispersant and detergent, and metallic dithiophosphate. Although evaluation of the additives was performed in lubricant formulations, these results correlate well with expected frictional and fuel economy improvements when these same additives are used in fuels burned in internal combustion engines. For example, this test generally predicts the reduction in friction of the piston rings moving against the cylinder walls that have been wetted by the additive blended into the fuel. The resulting reduction in friction observed, if any, may translate into an improvement in economy of the fuel actually consumed. Additionally, these additives when used in fuels, may actually help reduce wear of the internal combustion engine parts.

Description

The Low Velocity Friction Apparatus (LVFA) is used to measure the coefficient of friction of test lubricants under various loads, temperatures, and sliding speeds. The LVFA consists of a flat SEA 1020 steel surface (diameter 1.5 in.) which is attached to a drive shaft and rotated over a stationary, raised, narrow ringed SAE 1020 steel surface (area 0.08 in.$^2$. Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal the the coefficient of friction, is fed to the Y axis of an X—Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½HP electric motor. To vary the sliding speed, the output speed of the transmission is regulated by a lever-cammotor arrangement.

Procedure

The rubbing surfaces and 12–13 ml of test lubricants are placed on the LVFA. A 240 psi load is applied and the sliding speed is maintained at 40 fpm at ambient temperature for a few minutes. A plot for coefficients of friction ($U_k$) vs. speed were taken at 240, 300, 400, and 500 psi. Freshly polished steel specimens are used for each run. The surface of the steel is parallel ground to 4 to 8 microinches. The results in Table 1 refer to percent reduction infriction compared to the unmodified oil. That is, the formulation mentioned above was tested without the compound of this invention and this became the basis for comparison. The results were obtained at 250° F. and 500 psi.

TABLE 1

Evaluation of Frictional Properties Using the Low Velocity Friction Aparatus

| | Cont. in Test Oil Wt. % | Percent Reduction In Coefficient of Friction | |
|---|---|---|---|
| | | 5 Ft./Min. | 30 Ft./Min. |
| Base Oil A - Fully formulated synthetic automotive engine oil containing detergent/dispersant/ inhibitor performance package SAE 5W-30 | — | 0 | 0 |
| Example 2 - Plus Base Oil | 2 | 24 | 19 |

TABLE 2

Evaluation of Friction Properties Using Low Velocity Friction Apparatus

| | Concn. In Test Wt. % | Percent Reduction in Coefficient of Friction | |
|---|---|---|---|
| | | 5 Ft./Min. | 30 Ft./Min |
| Base Oil B - Fully formulated mineral oil based automotive engine oil containing detergent/dispersant/ inhibitor package - SAE 10W-40 | — | 0 | 0 |
| Example 2 - Plus Base Oil | 2 | 29 | 24 |

The high temperature oxidation stability of the additives was determined by evaluation of additive blends in 200 second solvent paraffinic neutral lubricating oil using the Catalytic Oxidation Test at 325° F. for 40 hours as shown in Table 3. In this test, air is passed through the lubricant sample containing small amounts of iron, copper, aluminum and lead at the temperature and for the time mentioned.

TABLE 3

CATALYST OXIDATION TEST
325° F., 40 hours

| | Conc. in Test Oil, Wt. % | Viscosity Increase Measured at 100° C., % | Neutralization Number |
|---|---|---|---|
| Base Oil - 200" solvent Parafinic Neutral Lube Oil | — | 67 | 3.62 |
| Example 2 in above base oil | 0.5 | 13 | 3.06 |

The copper strip corrosivity of Example 2 was evaluated using ASTM D130-80 as shown in Table 4. As shown by the results, the product was relatively non-corrosive to copper.

TABLE 4

| | Copper Strip Corrosivity | | |
|---|---|---|---|
| Example | Conc, Wt. % 200"SPN Lubricating Oil | ASTM D130-80 210° F., 6 Hrs | ASTM D13-80 250° F., 3 Hrs |
| 2 | 0.5 | 1A | 1B |

I claim:

1. A product of reaction made by (1) reacting a boron compound selected from the group consisting of boric oxide, a metaborate, a compound of the formula $$(RO)_xB(OH)_y$$

wherein R is a $C_1$ to $C_6$ alkyl group and x and y are 0 to 3, their sum being 3, and mixtures thereof, with an amine or mixture of amines of the formula $$R-NH-R^1-NH-R^1-NHR$$

wherein R is hydrogen or a $C_{10}$ to $C_{30}$ hydrocarbyl group, at least one R being the latter and $R^1$ is the same of different $C_2$ to $C_4$ hydrocarbylene group, followed by (2) reacting the product of (1) with a carboxylic acid of ester of the formula $$R^2COOR^3$$

wherein $R^2$ and $R^3$ are individually hydrogen or a $C_1$ to $C_4$ hydrocarbyl group, the amount of boron compound reacted with the amine being sufficient to react from about 5% to about 95% of the available amino groups, and the amount of acid or ester reacted with product (1) being sufficient to react from about 5% to about 100% of the unborated sites.

2. The product of claim 1 wherein R is hydrogen, alkyl, alkenyl, aryl, alkaryl, aralkyl or cycloalkyl, and wherein at least one R is not hydrogen.

3. The product of claim 1 wherein $R^1$ is an ethylene group, a propylene group or a butylene group.

4. The product of claim 1 wherein $R^2$ and $R^3$ are individually a $C_1$ to $C_4$ hydrocarbyl group.

5. The product of claim 4 wherein the hydrocarbyl group is a methyl, ethyl, propyl or butyl group.

6. The product of claim 1 wherein the amine is N-oleyl diethylenetriamine, N-tallow diethylenetriamine, N-hydrogenated tallow diethylenetriamine, N-soya diethylenetriamine, N-coco diethylenetriamine, N-decyl diethylenetriamine, N-dodecyl diethylenetriamine, N-tetradecyl diethylenetriamine, N-octadecyl diethylenetriamine, N-eicosyl diethylenetriamine, N-triacontyl diethylenetriamine, N-oleyl dipropylenetriamine, N-tallow dipropylenetriamine, N-hydrogenated tallow dipropylenetriamine, N-soya dipropylenetriamine, N-coco dipropylenetriamine, N-decyl dipropylenetriamine, N-dodecyl dipropylenetriamine, N-tetradecyl dipropylenedtriamine, N-octadecyl dipropylenetriamine, N-eicosyl dipropylenetriamine, N-triacontyl dipropylenetriamine, the corresponding $N-C_{10}$ to $C_{30}$ hydrocarbyl dibutylenetriamine members, mixed $N-C_{10}$ to $C_{30}$ hydrocarbyl ethylenepropylenetriamine, $N-C_{10}$ to $C_{30}$ hydrocarbyl ethylenebutylenetriamine or mixed $N-C_{10}$ to $C_{30}$ hydrocarbyl propylenebutylenetriamine.

7. The product of claim 5 wherein the acid is formic acid, acetic acid, propionic acid, butyric acid or mixtures thereof.

8. The product of claim 1 wherein the boron compound is a metaborate, boric oxide, boric acid, mono-, di- or trimethyl borate, mono-, di- or triethyl borate, mono-, di- or tripropyl borate, mono-, di- or tributyl borate, mono-, di- or triamyl borate or mono-, di- or trihexyl borate.

9. The product of claim 8 wherein the boron compound is boric acid.

10. The product of claim 1 wherein the amine is N-tallow-dipropylenetriamine, the boron compound is boric acid and the carboxylic acid is formic acid.

11. A lubricant composition comprising a major amount of a lubricating oil or grease therefrom and an antifriction amount of product of reaction made by (1) reacting a boron compound selected from the group consisting of boric oxide, a metaborate, a compound of the formula $$(RO)_xB(OH)_y$$

wherein R is a $C_1$ to $C_6$ alkyl group and x and y are 0 to 3, their sum being 3, and mixtures thereof, with an amine or mixture of amines of the formula $$R-NH-R^1-NH-R^1-NHR$$

wherein R is hydrogen or a $C_{10}$ to $C_{30}$ hydrocarbyl group, at least one R being the latter and $R^1$ is the same of different $C_2$ to $C_4$ hydrocarbylene group, followed by (2) reacting the product of (1) with a carboxylic acid of ester of the formula $$R^2COOR^3$$

wherein $R^2$ and $R^3$ are individually hydrogen or a $C_1$ to $C_4$ hydrocarbyl group, the amount of boron compound reacted with the amine being sufficient to react from about 5% to about 95% of the available amino groups, and the amount of acid or ester reacted with product (1) being sufficient to react from about 5% to about 100% of the unborated sites.

12. The composition of claim 11 wherein R is hydrogen, alkyl, alkenyl, aryl, alkaryl, aralkyl or cycloalkyl, and wherein at least one R is not hydrogen.

13. The composition of claim 11 wherein $R^1$ is an ethylene group, a propylene group or a butylene group.

14. The composition of claim 11 wherein $R^2$ and $R^3$ are individually a $C_1$ to $C_4$ hydrocarbyl group.

15. The composition of claim 14 wherein the hydrocarbyl group is a methyl, ethyl, propyl or butyl group.

16. The composition of claim 11 wherein the amine is N-oleyl diethylenetriamine, N-tallow diethylenetriamine, N-hydrogenated tallow diethylenetriamine, N-soya diethylenetriamine, N-coco diethylenetriamine, N-decyl diethylenetriamine, N-dodecyl diethylenetriamine, N-tetradecyl diethylenetriamine, N-octadecyl diethylenetriamine, N-eicosyl diethylenetriamine, N-triacontyl diethylenetriamine, N-oleyl dipropylenetriamine, N-tallow dipropylenetriamine, N-hydrogenated tallow dipropylenetriamine, N-soya dipropylenetriamine, N-coco dipropylenetriamine, N-decyl dipropylenetriamine, N-dodecyl dipropylenetriamine, N-tetradecyl dipropylenedtriamine, N-octadecyl dipropylenetriamine, N-eicosyl dipropylenetriamine, N-triacontyl dipropylenetriamine, the corresponding N—$C_{10}$ to $C_{30}$ hydrocarbyl dibutylenetriamine members, mixed N—$C_{10}$ to $C_{30}$ hydrocarbyl ethylenepropylenetriamine, N—$C_{10}$ to $C_{30}$ hydrocarbyl ethylenebutylenetriamine or mixed N—$C_{10}$ to $C_{30}$ hydrocarbyl propylenebutylenetriamine.

17. The composition of claim 15 wherein the acid is formic acid, acetic acid, propionic acid, butyric acid or mixtures thereof.

18. The composition of claim 11 wherein the boron compound is a metaborate, boric oxide, boric acid, mono-, di- or trimethyl borate, mono-, di- or triethyl borate, mono-, di- or tripropyl borate, mono-, di- or tributyl borate, mono-, di- or triamyl borate or mono-, di- or trihexyl borate.

19. The composition of claim 18 wherein the boron compound is boric acid.

20. The composition of claim 11 wherein the amine is N-tallow-dipropylenetriamine, the boron compound is boric acid and the carboxylic acid is formic acid.

21. The composition of claim 11 wherein the lubricant is (1) a mineral oil, (2) a synthetic oil or a mixture of synthetic oils, (3) a mixture of (1) and (2) and (4) a grease from (1), (2) or (3).

22. The composition of claim 21 wherein the lubricant is a mineral oil.

23. The composition of claim 21 wherein the lubricant is a synthetic oil or mixture of synthetic oils.

24. The composition of claim 21 wherein the lubricant is a mixture of (1) and (2).

25. The composition of claim 21 wherein the lubricant is said grease.

26. The composition of claim 25 wherein said grease is thickened using at least 1% by weight of a metal hydroxycarboxylate.

27. The composition of claim 11 additionally containing one or more of a group consisting of a phenate, a sulfonate, a succinimide and a zinc dialkyl dithiophosphate.

28. A method of reducing fuel consumption in an internal combustion engine comprising (1) lubricating said engine with a lubricating oil composition comprising a major proportion of a lubricating oil and a fuel consumption reducing amount of a product of reaction made by (A) reacting a boron compound selected from the group consisting of boric oxide, a metaborate, a compound of the formula $$(RO)_x B(OH)_y$$

wherein R is a $C_1$ to $C_6$ alkyl group and x and y are 0 to 3, their sum being 3, and mixtures thereof, with an amine or mixture of amines of the formula $$R-NH-R^1-NH-R^1-NHR$$

wherein R is hydrogen or a $C_{10}$ to $C_{30}$ hydrocarbyl group, at least one R being the latter and $R^1$ is the same of different $C_2$ to $C_4$ hydrocarbylene group followed by (B) reacting the product of (A) with a carboxylic acid of ester of the formula $$R^2 COOR^3$$

wherein $R^2$ and $R^3$ are individually hydrogen or a $C_1$ to $C_4$ hydrocarbyl group, the amount of boron compound reacted with the amine being sufficient to react from about 5% to about 95% of the available amino groups, and the amount of acid or ester reacted with product (1) being sufficient to react from about 5% to about 100% of the unborated sites.

* * * * *